(12) United States Patent
Watanabe et al.

(10) Patent No.: US 6,825,996 B2
(45) Date of Patent: Nov. 30, 2004

(54) SAMPLE INSPECTING CASING

(75) Inventors: Yasuhiro Watanabe, Saitama (JP); Isamu Kaneko, Saitama (JP)

(73) Assignee: Enplas Corporation, Saitama (JP)

( * ) Notice: Subject to any disclaimer, the term of this patent is extended or adjusted under 35 U.S.C. 154(b) by 0 days.

(21) Appl. No.: 10/402,495

(22) Filed: Mar. 28, 2003

(65) Prior Publication Data

US 2003/0189702 A1 Oct. 9, 2003

(30) Foreign Application Priority Data

Apr. 3, 2002 (JP) .................................... P2002-101769

(51) Int. Cl.[7] .......................... G02B 7/02; G02B 27/00; G02B 27/02; G01N 21/00; G01N 21/01
(52) U.S. Cl. ...................... 359/810; 359/800; 359/801; 359/808; 356/244; 356/237.1
(58) Field of Search ................................. 359/800–802, 359/804, 808–810, 819; 356/426, 427, 237.1–237.6, 239.6–239.8, 244; 362/138, 154, 317, 351, 355, 375

(56) References Cited

U.S. PATENT DOCUMENTS 5,585,808 A * 12/1996 Wysome ...................... 343/703
6,280,048 B1 * 8/2001 Luquire ....................... 362/125
6,392,745 B1 * 5/2002 Mavliev et al. ................ 356/37

* cited by examiner

Primary Examiner—Hung Xuan Dang
Assistant Examiner—Joseph Martinez
(74) Attorney, Agent, or Firm—Bachman & LaPointe, P.C.

(57) ABSTRACT

There is provided a sample inspection casing capable of easily and surely inspecting an object to be inspected. The sample inspection casing 1 includes: a sample mounting table 5 for mounting thereon an object 11 to be inspected; a prism cut portion 14 serving as an optical path changing portion for allowing the object 11 on the sample mounting table 5 to be irradiated with illuminating light; and an image magnifying lens 15 for transmitting light, which is reflected on the object 11 on the sample mounting table 5, to magnify an image of the object 11.

17 Claims, 6 Drawing Sheets

SAMPLE INSPECTING CASING

BACKGROUND OF THE INVENTION

1. Field of the Invention

The present invention generally relates to a sample inspection casing. More specifically, the invention relates to a sample inspection casing used for inspecting an object to be inspected, such as an IC device, with the naked eye.

2. Description of the Prior Art

When a current-carrying test, such as a burn-in test, is carried out with respect to an IC device serving as an object to be inspected, there are some cases where the IC device contacts a contact pin of an IC socket to makes flaws on the surface of the device or a connecting terminal, or that a pressing member, such as a latch or a heat sink, makes flaws, such as impressions, on the surface of the device when the device is pressed on an IC socket to be fixed thereto. The degree of the flaws is checked by operator's eyes after the current-carrying test is completed.

However, when the flaws on the IC device are checked, the flaws themselves are very small, so that there are some cases where it is difficult to determine whether flaws are made or foreign matters, such as metal powder, adhere thereto. In such cases, if the surface of the IC device to be observed can be washed or cleaned, or if the cleaned surface to be observed can be irradiated with illuminating light to be magnified to be viewed, the operator can easily and surely check flaws on the IC device.

SUMMARY OF THE INVENTION

It is therefore an object of the present invention to eliminate the aforementioned problems and to provide a sample inspection casing capable of easily and surely inspecting an object to be inspected, such as an IC device.

In order to accomplish the aforementioned and other objects, according to one aspect of the present invention, a sample inspection casing comprises: a sample mounting portion for mounting thereon an object to be inspected; optical path changing means for allowing the object on the sample mounting portion to be irradiated with illuminating light; and an image magnifying lens for transmitting light, which is reflected on the object on the sample mounting portion, to magnify an image of the object.

According to another aspect of the present invention, a sample inspection casing comprises: a casing first half having a sample mounting portion for mounting thereon an object to be inspected; a casing second half having optical path changing means for allowing the object on the sample mounting portion to be irradiated with illuminating light, the casing second half having an image magnifying lens for transmitting light, which is reflected on the object on the sample mounting portion, to magnify an image of the object; and a hinge portion connecting the casing first half to the casing second half so as to allow the casing first half and the casing second half to be open and closed, wherein the sample mounting portion is arranged in a closed space defined by the casing first half and the casing second half when the casing first half and the casing second half are closed.

In this sample inspection casing, the casing first half may have a space for housing therein an excess of a coating liquid which is coated on the object mounted on the sample mounting portion.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of the present invention will be described below.

[First Preferred Embodiment]

Figure 1:
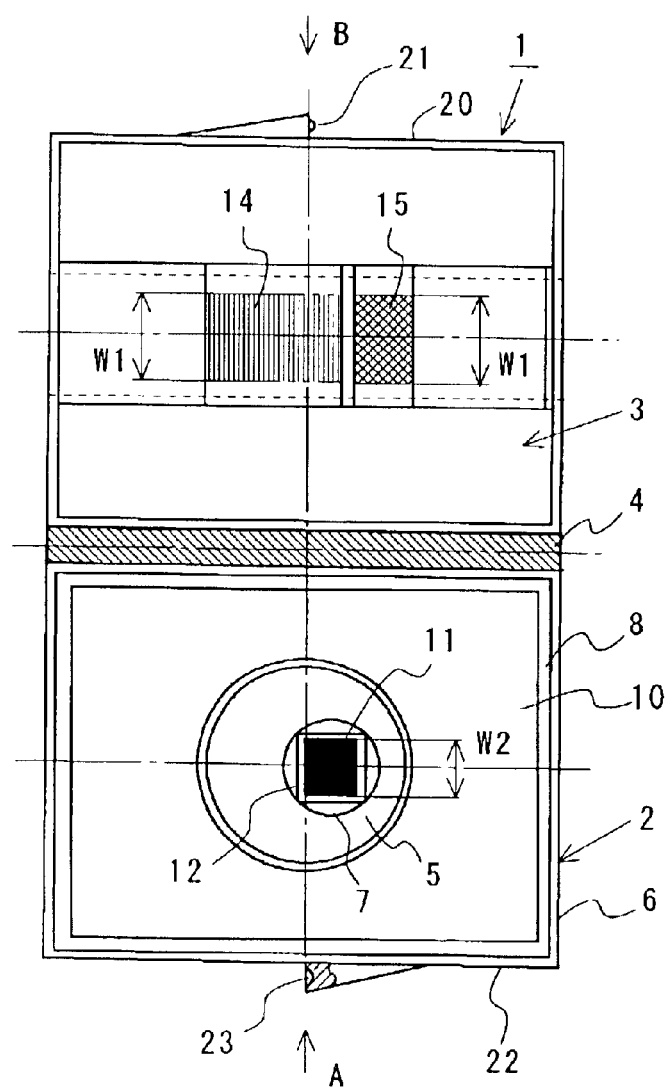
FIG. 1 is a plan view of the first preferred embodiment of a sample inspection casing according to the present invention when it is open.
Figure 2:
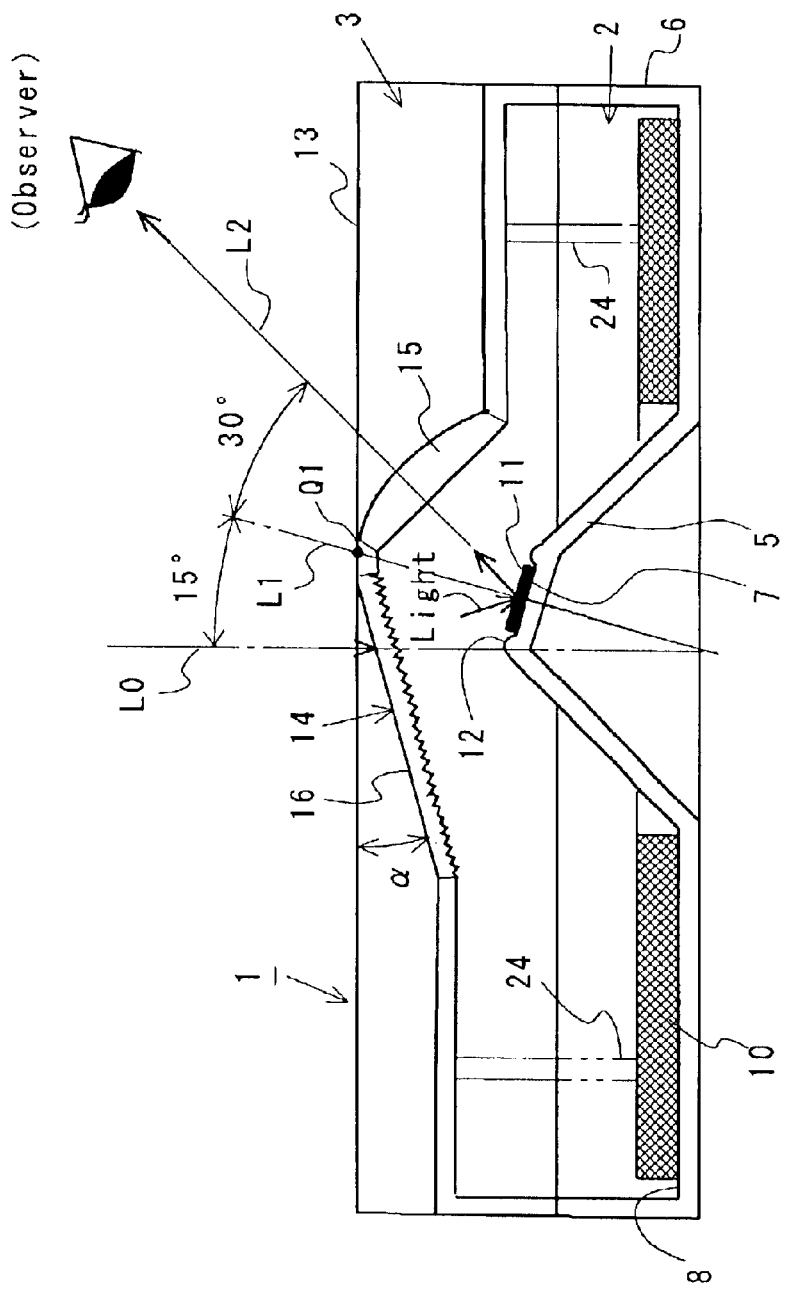
FIG. 2 is a vertically sectional view of the first preferred embodiment of a sample inspection casing according to the present invention when it is closed.
Figure 3:
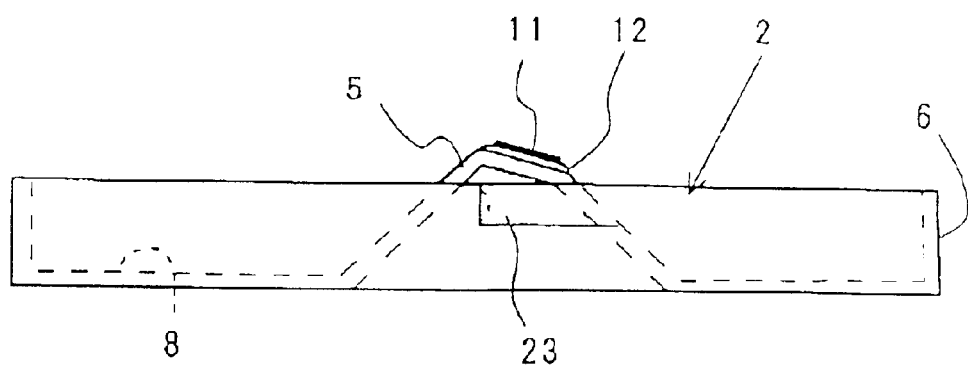
FIG. 3 is a side view which is viewed in a direction of arrow A in FIG. 1.
Figure 4:
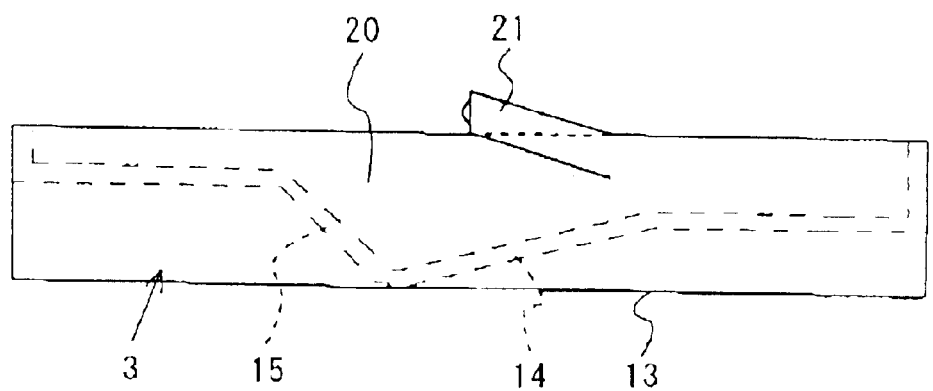
FIG. 4 is a side view which is viewed in a direction of arrow B in FIG. 1.

FIGS. 1 through 4 show the first preferred embodiment of a sample inspection casing 1 according to the present invention. FIG. 1 is a plan view showing a state that a casing lower half 2 and a casing upper half 3 are open, and FIG. 2 is a sectional view showing a state that the casing upper half 3 lies on the casing lower half 2 so that the casing upper half 3 and the casing lower half 2 are closed. FIG. 3 is a side view which is viewed in a direction of arrow A of FIG. 1, and FIG. 4 is a side view which is viewed in a direction of arrow B of FIG. 1.

As shown in these figures, the sample inspection casing 1 comprises the casing lower half 2, and the casing upper half 3 which is connected to the casing lower half 2 by means of a hinge portion 4 so that the casing upper half 3 and the casing lower half 2 can be open and closed about the hinge portion 4. The casing upper half 3 is formed of a transparent resin material which allows observation from the outside, and the casing lower half 2 is formed of a chemical resistant resin material capable of housing and holding therein a cleaning solution and/or a reagent. The casing upper half 3 may be formed of a transparent resin material, through which at least a prism cut portion 14 and an image magnifying lens 15, which will be described later, can be observed from the outside. If no cleaning solution and reagent are used or if it is not required to consider chemical resistance, the whole sample inspection casing 1 may be integrally formed of the transparent resin material for the casing upper half 3.

The casing lower half 2 has a depth (space) so as to be capable of sufficiently housing therein an excess of a liquid (coating liquid), such as a cleaning solution or a reagent. The casing lower half 2 is formed so that a sample mounting table 5 protrudes upwards in a substantially central portion to be higher than the height of side walls 6 (see FIGS. 2 and 3). The sample mounting table 5 of the casing lower half 2 has a shape which is formed by obliquely cutting the tip portion of a substantially conical shape. As shown in FIG. 2, a sample mounting surface 7 of the sample mounting table 5 is inclined by about 15 degrees. That is, the sample mounting surface 7 is inclined so that an angle between the vertical center line L0 of the sample inspection casing 1 and the normal L1 of the sample mounting surface 7 is about 15 degrees. A waste liquid absorber 10 is designed to be fixed (e.g. bonded) to the bottom face 8 of the casing lower half 2 so as to be capable of absorbing a waste liquid (excessive coating liquid) of the cleaning solution and/or reagent which is coated on an inspecting object 11 mounted on the sample mounting table 5. If a positioning protrusion 12 for positioning the inspecting object 11, such as an IC package, is formed on the sample mounting surface 7 and if the inspecting object 11 engages the positioning protrusion 12, even if the sample inspection casing 1 is tilted, the inspecting object 11 does not slide and fall from the sample mounting surface 7.

As shown in FIG. 2, the casing upper half 3 has a prism cut portion 14 serving as an optical path changing means which extends from a vicinity of an intersection Q1 between the normal L1 of the central portion of the sample mounting table 5 and a top face 13 of the casing upper half 3 and which is inclined so that an angle α between the top face 13 and the prism cut portion 14 is about 15 degrees. The casing upper half 13 also has an image magnifying lens 15 which is formed so that the center line L2 of the lens 15 crosses the normal L1 of the central portion at an inclined angle of about 30 degrees. The prism cut portion 14 is designed to change the traveling direction of light, which travels in a vertical direction from top to bottom in FIG. 2, toward the surface of the inspecting object 11, so that light from an illuminating means, such as an indoor fluorescent lamp, can be efficiently utilized as illuminating light for the inspecting object 11. The image magnifying lens 15 is designed to transmit light, which is reflected on the surface of the inspecting object 11, to form a magnified image on observer's retinas. Furthermore, in FIG. 1, the prism cut portion 14 and the image magnifying lens 15 are formed so as to have a width W1 which is greater than at least the width W2 of the inspecting object 11.

Figure 5:
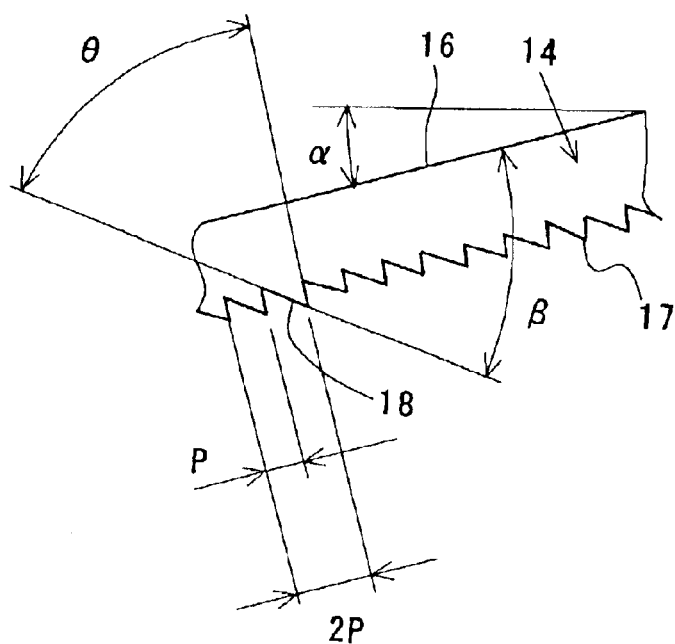
FIG. 5 is an enlarged view of a part of a prism cut portion of the first preferred embodiment of a sample inspection casing according to the present invention.

As shown in FIG. 5 in detail, the top face 16 of the prism cut portion 14 is formed as a mirror finished surface so that the angle a between the top face 16 and the top face 13 of the casing upper half 3 is about 15 degrees. On the whole bottom face of the prism cut portion 14, a large number of minute protrusions 17 are formed at regular intervals (pitch P). Each of the minute protrusions 17 of the prism cut portion 14 has a substantially triangular cross section which has a vertical angle θ (e.g. about 61 degrees) and an inclined face 18 which is inclined by β (e.g. about 29 degrees) from the top face 16 of the prism cut portion 14.

If the casing upper half 3 rotates about the hinge portion 4 to lie on the casing lower half 2 to allow an engaging protruding portion 21, which is formed on the side of the side face 20 of the casing upper half 3, to engage an engaged recessed portion 23 which is formed on the side of the side face 22 of the casing lower half 2, the casing upper half 3 can lie on the casing lower half 2 to be closed, so that the inspecting object 11 mounted on the sample mounting table 5 can be housed and held in the closed space defined by the casing lower half 2 and the casing upper half 3. Furthermore, as shown in FIG. 2, absorber pressing ribs 24 may be formed on the surface of the casing upper half 3 facing the casing lower half 2 so that the waste liquid absorber 10 is pressed and fixed to the bottom face 8 of the casing lower half 2 by the absorber pressing ribs 24 when the casing upper half 3 lies on the casing lower half 2.

With this construction, the sample inspection casing 1 in this preferred embodiment allows the inspecting object 11 to be mounted on the sample mounting surface 7 of the sample mounting table 5 when the casing upper half 3 is open. Thereafter, a liquid, such as a cleaning solution and/or a reagent is coated to the surface of the inspecting object 11 to be observed. At this time, an excess of the liquid falling from the sample mounting table 5 collects on the bottom portion of the casing lower half 2 to be absorbed into the waste liquid absorber 10. Then, the casing upper half 3 is arranged so as to lie on the casing lower half 2, and the engaging protruding portion 21 of the casing upper half 3 is caused to engage the engaged recessed portion 23 of the casing lower case 2. Thus, the inspecting object 11 is housed and held on the sample mounting table 5 in the closed space defined by the casing lower half 2 and casing upper half 3. Then, the observer (operator) holds the sample inspection casing 1 in this state to allow the inspecting casing 11 on the sample mounting table 5 to be irradiated with light from an illuminating means, such as a fluorescent lamp, via the prism cut portion 14, to observe light, which is reflected on the inspecting object 11, via the image magnifying lens 15.

According to this preferred embodiment, since the inspecting object 11, on which the cleaning solution and/or the reagent are coated and from which foreign matters on the surface to be observed are removed, can be housed and held in the closed space defined by the casing lower half 2 and casing upper half 3, it is possible to accurately inspect the inspecting object 11 without allowing wastes or contaminations and impurities in the atmosphere from adhering the surface of the inspecting object to be observed when observation is carried out.

According to this preferred embodiment, since the inspecting object 11 on the sample mounting table 5 can be efficiently irradiated with light via the prism cut portion 14 to observe its reflected light via the image magnifying lens 15, the surface of the inspecting object 11 to be observed can be magnified to be viewed, so that it is possible to easily inspect the inspecting object 11.

For example, if the sample inspection casing 1 in this preferred embodiment is used for inspecting flaws on an IC device serving as the inspecting object 11, it is possible to easily and accurately observe the degree of flaws on the IC device. Even if the sample inspection casing 1 in this preferred embodiment is used for optically inspecting a reaction of an inspecting object 11 other than IC devices with a reagent (e.g. for observing the color of the inspecting object 11), it is possible to easily and accurately inspect the inspecting object 11.

According to this preferred embodiment, since the waste liquid absorber 10 is arranged in the casing lower half 2, the excessive coating liquid of the cleaning solution and/or reagent is absorbed into the waste liquid absorber 10, so that the excessive coating liquid does not leak out of the sample inspection casing 1 to the outside.

While the prism cut portion 14 has been described as an example of an optical path changing means in this preferred embodiment, the present invention should not be limited thereto, but the optical path may be changed by a lens or a reflecting mirror.

While the sample mounting table 5 has been formed by obliquely cutting the tip portion of the substantially conical shape in this preferred embodiment, the present invention should not be limited thereto, but the sample mounting table 5 may be formed by obliquely cutting the tip portion of a pyramid.

While the casing upper half 3 serving as a lid and the casing lower half 2 have been integrally formed by, e.g., the injecting molding, so as to be connected to each other by means of the hinge portion 4 in this preferred embodiment, the present invention should not be limited thereto, but the casing lower half 2 and the casing upper half 3 may be separately formed.

While illuminating light, such as light of a fluorescent lamp or solar light, has been designed to enter the prism cut portion 14 in this preferred embodiment, a light source, such as a light emitting diode (LED), may be mounted on the casing upper half 3 so as to use light from the light source as illuminating light. Thus, even if illuminating light having sufficient brightness can not be obtained by only indoor lamps and/or natural light, illumination brightness can be sufficient so that the inspecting object 11 can be inspected with the naked eye.

Figure 6:
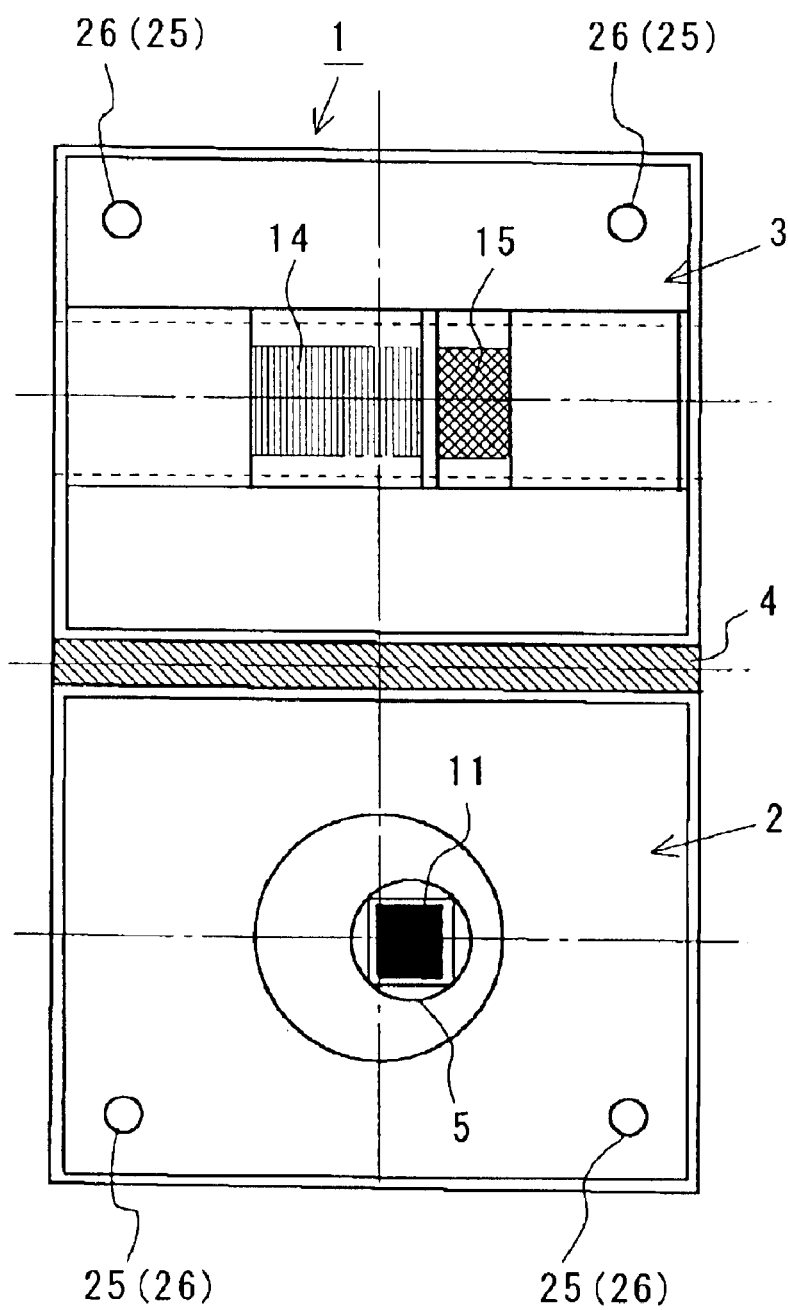
FIG. 6 is a plan view of a modified example of the first preferred embodiment of a sample inspection casing according to the present invention.

While the engaging protruding portion 21 and the engaged recessed portion 23 have been used as means for fixing the casing upper half 3 to the casing lower half 2 while closing the casing upper half 3 in this preferred embodiment, the present invention should not be limited thereto, but any means may be used if the casing lower half 2 and the casing upper half 3 can be held when they are closed. For example, a rubber band may be wound onto the closed casing lower half 2 and casing upper half 3 to hold the closed casing lower half 2 and casing upper half 3. Alternatively, as shown in FIG. 6, rod-like protrusions 25 formed on one of the casing lower half 2 and casing upper half 3 may engage holes 26 formed in the other of the casing lower half 2 and casing upper half 3 so that the casing upper half 3 is held on the casing lower half 2 by frictional resistance between the rod-like protrusions 25 and the holes 26.

If the sample mounting table 5 has a fixing means for fixing the inspecting object 11 to the sample mounting table 5 in this preferred embodiment, even if strong shocks are applied to the sample inspection casing 1, e.g. even if the sample inspection casing 1 falls from a desk, the inspecting object 11 can be surely fixed to the sample mounting table 5 without falling from the sample mounting table 5.

Such a fixing means may be formed by preparing a transparent plate-like lid substantially having the same size as that of the sample mounting surface 7 of the sample mounting table 5, rotatably mounting one end of the lid on the sample mounting table 5, and detachably mounting the other end of the lid on the sample mounting table 5, although this is not shown. With this construction, after the inspecting object 11 is mounted on the sample mounting surface 7 of the sample mounting table 5, if the lid is rotated so as to lie on the sample mounting surface 7, and if the other end of the lid is engaged with the sample mounting table 5, the lid can cover the sample mounting surface 7, and the inspecting object 11 can be fixed to the sample mounting table 5. In this case, since there are some cases where illuminating light from the prism cut portion 14 is reflected on the surface of the lid so that it is difficult to observe the surface of the inspecting object 11, a reflection reducing coating is preferably formed on the surface of the lid.

Alternatively, the fixing means may be a pressure sensitive adhesive double coated tape, applied on the sample mounting surface 7, for fixing the inspecting object 11 thereto.

In this preferred embodiment, the angles and sizes of the respective portions have been described as examples, and may be set to be optimum numerical values in accordance with the type of the inspecting object 11 and working conditions.

[Second Preferred Embodiment]

Figure 7:
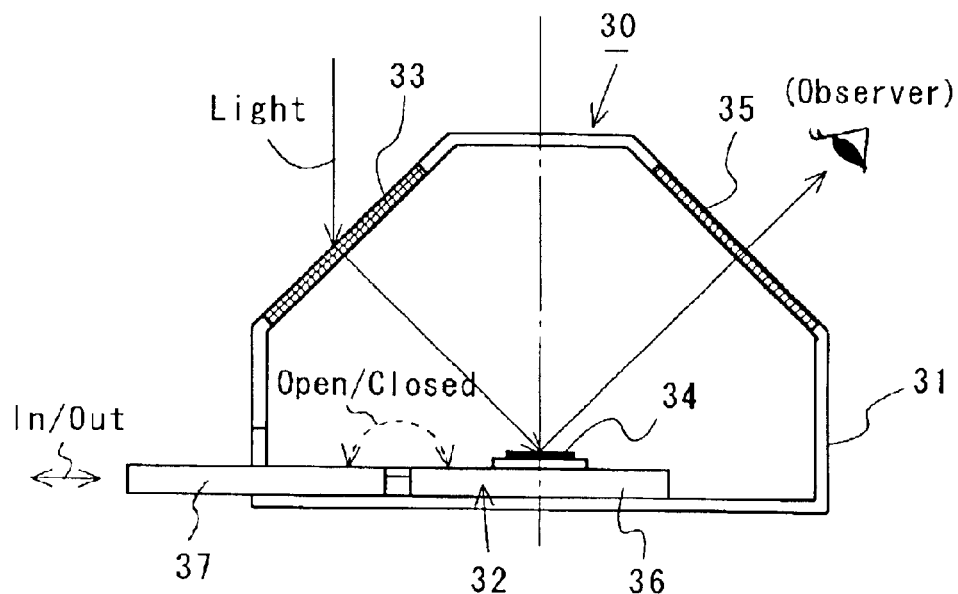
FIG. 7 is a vertically sectional view of the second preferred embodiment of a sample inspection casing according to the present invention.
Figure 8:
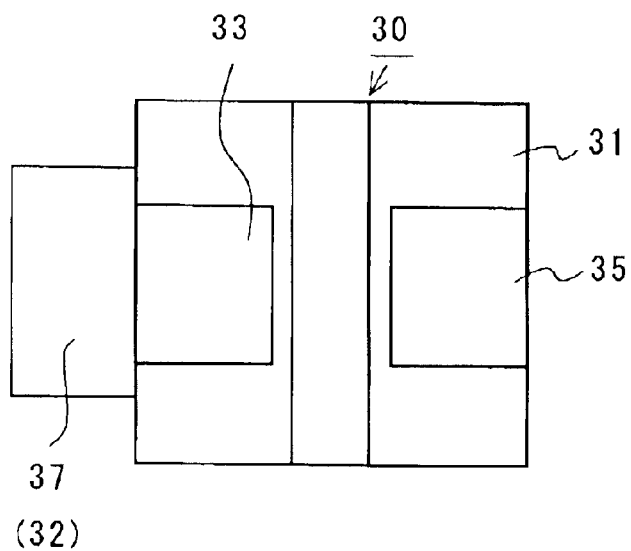
FIG. 8 is a plan view of the second preferred embodiment of a sample inspection casing according to the present invention.

FIGS. 7 and 8 shows the second preferred embodiment of a sample inspection casing 30 according to the present invention. As shown in these figures, the sample inspection casing 30 in this preferred embodiment has a sample mounting table 32 capable of being carried in and out of a casing body 31. An inspecting object 34 mounted on the sample mounting table 32 is irradiated with light entering the casing body 31 through a prism cut portion 33 of the casing body 31, and light reflected on the inspecting body 34 leaves the casing body 31 via an image magnifying lens 35 to the outside, so that an observer can observe an image magnified by the image magnifying lens 35.

The sample mounting table 32 has a lid 37 capable of closing the inspecting object 34 on a lower mounting table 36. Thus, when the sample mounting table 32 is stored outside of the casing body 31, the lower mounting table 36 is covered with the lid 37, so that it is possible to prevent floating wastes or contaminations and impurities from adhering to the surface of the inspecting object 34. On the other hand, when the inspecting object 34 is inspected and when the sample mounting table 32 is inserted into the casing body 31, the lid 37 is open to expose the inspecting object 34. Therefore, in the sample inspection casing 30 in this preferred embodiment as compared with the sample inspection casing 1 in the first preferred embodiment wherein the casing lower half 2 and the casing upper half 3 are always closed to be treated (inspect), impurities and floating wastes or contaminations are easy to adhere to the inspecting object 34, so that it is required to be sufficiently careful about adhesion of wastes and so forth to the inspecting object 34 when the sample mounting table 32 is inserted into the casing body 31.

Since the sample inspection casing 30 in this preferred embodiment is formed so as to allow the sample mounting table 32 to be carried in and out thereof, the whole size thereof is larger than that in the first preferred embodiment. Therefore, the sample inspection casing 30 in this preferred embodiment can be effectively used when storage and inspection places can be sufficiently ensured.

According to the sample inspection casing 30 in this preferred embodiment with such a construction, it is possible to easily and surely inspect the surface of the inspecting object 34 similar to the first preferred embodiment.

As described above, according to the present invention, the inspecting object is mounted on the sample mounting table to allow the surface of the inspecting object to be irradiated with illuminating light via the optical path changing means, and light reflected on the inspecting object passes through the image magnifying lens, so that the surface of the inspecting object can be magnified to be observed while being brightly illuminated. Therefore, according to the present invention, it is possible to easily and surely inspect the inspecting object.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A sample inspection casing comprising:

a casing first half;

a casing second half connected to said casing first half for defining a closed space therein;

a sample mounting portion, provided on said casing first half, for mounting thereon an object to be inspected in said closed space;

optical path changing means, provided on said casing second half, for receiving light from the outside of said closed space to change a traveling direction of the received light to allow said object on said sample mounting portion to be irradiated with light; and an image magnifying lens, provided on said casing second half, for transmitting light, which is reflected on said object on said sample mounting portion, to magnify an image of the object.

2. A sample inspection casing as set forth in claim 1, wherein said optical path changing means changes a traveling direction of light, which travels in a vertical direction from top to bottom, toward a surface of said object.

3. A sample inspection casing as set forth in claim 1, wherein said sample mounting portion is formed so as to allow said light, which is reflected on said object on said sample mounting portion, to be transmitted toward said image magnifying lens.

4. A sample inspection casing as set forth in claim 1, wherein said optical path changing means comprises a prism cut portion which has a top face formed as a mirror finished surface and which has a bottom face having protrusions at regular intervals.

5. A sample inspection casing as set forth in claim 4, wherein said protrusions have a substantially triangular cross section.

6. A sample inspection casing comprising:

a casing first half having a sample mounting portion for mounting thereon an object to be inspected;

a casing second half having optical path changing means for changing a traveling direction of light to allow said object on said sample mounting portion to be irradiated with illuminating light, said casing second half having an image magnifying lens for transmitting light, which is reflected on said object on said sample mounting portion, to magnify an image of the object; and a hinge portion connecting said casing first half to said casing second half so as to allow said casing first half and said casing second half to be open and closed, wherein said sample mounting portion is arranged in a closed space defined by said casing first half and said casing second half when said casing first half and said casing second half are closed.

7. A sample inspection casing as set forth in claim 6, wherein said casing first half has a space for housing therein an excess of a coating liquid which is coated on said object mounted on said sample mounting portion.

8. A sample inspection casing as set forth in claim 6, wherein said optical path changing means changes a traveling direction of light, which travels in a vertical direction from top to bottom, toward a surface of said object.

9. A sample inspection casing as set forth in claim 6, wherein a top face of said sample mounting portion, on which said object is mounted, is inclined so as to allow said light, which is reflected on said object on said sample mounting portion, to be transmitted toward said image magnifying lens.

10. A sample inspection casing as set forth in claim 6, wherein said optical path changing means comprises a prism cut portion which has a top face formed as a mirror finished surface and which has a bottom face having protrusions at regular intervals.

11. A sample inspection casing as set forth in claim 10, wherein said protrusions have a substantially triangular cross section.

12. A sample inspection casing comprising:

a casing first half;

a casing second half for opening and closing said casing first half so that a closed space is defined when said casing first halt is closed by said casing second half;

a hinge portion connecting said casing first half to said casing second half so as to allow said casing second half to open and close said casing first half;

a sample mounting portion, provided on said casing first half and arranged in said closed space, for supporting thereon an object to be inspected;

optical path changing means, provided on said casing second half, for changing a traveling direction of light to allow said object on said sample mounting portion to be irradiated with illuminating light; and an image magnifying lens for transmitting light, which is reflected on said object on said sample mounting portion, to magnify an image of the object.

13. A sample inspection casing as set forth in claim 12, wherein said optical path changing means changes a traveling direction of light, which travels in a vertical direction from top to bottom, toward a surface of said object.

14. A sample inspection casing as set forth in claim 12, wherein said casing first half has a space for housing therein an excess of a coating liquid which is coated on said object mounted on said sample mounting portion.

15. A sample inspection casing as set forth in claim 12, wherein a top face of said sample mounting portion, on which said object is mounted, is inclined so as to allow said light, which is reflected on said object on said sample mounting portion, to be transmitted toward said image magnifying lens.

16. A sample inspection casing as set forth in claim 12, wherein said optical path changing means comprises a prism cut portion which has a top face formed as a mirror finished surface and which has a bottom face having protrusions at regular intervals.

17. A sample inspection casing as set forth in claim 16, wherein said protrusions have a substantially triangular cross section.

* * * * *